United States Patent
Cohen et al.

(10) Patent No.: US 9,545,389 B2
(45) Date of Patent: Jan. 17, 2017

(54) BACLOFEN AND ACAMPROSATE BASED THERAPY OF MACULAR DEGENERATION DISORDERS

(71) Applicant: PHARNEXT, Issy les Moulineaux (FR)

(72) Inventors: Daniel Cohen, Saint Cloud (FR); Ilya Chumakov, Vaux Le Penil (FR); Serguei Nabirochkin, Chatenay Malabry (FR)

(73) Assignee: Pharnext, Issy les Moulineaux (FR)

( * ) Notice: Subject to any disclaimer, the term of this patent is extended or adjusted under 35 U.S.C. 154(b) by 0 days.

(21) Appl. No.: 14/415,994

(22) PCT Filed: Jul. 18, 2013

(86) PCT No.: PCT/EP2013/065209
§ 371 (c)(1),
(2) Date: Jan. 20, 2015

(87) PCT Pub. No.: WO2014/013025
PCT Pub. Date: Jan. 23, 2014

(65) Prior Publication Data
US 2015/0238452 A1    Aug. 27, 2015

Related U.S. Application Data (60) Provisional application No. 61/672,893, filed on Jul. 18, 2012.

(51) Int. Cl.
*A61K 31/185* (2006.01)
*A61K 31/197* (2006.01)

(52) U.S. Cl.
CPC ........... *A61K 31/197* (2013.01); *A61K 31/185* (2013.01)

(58) Field of Classification Search
CPC ........................... A61K 31/197; A61K 31/185
See application file for complete search history.

(56) References Cited

U.S. PATENT DOCUMENTS

| 8,741,886 B2 * | 6/2014 | Cohen ................. A61K 31/137 514/183 |
| 8,865,769 B2 * | 10/2014 | Cohen ........................... 514/555 |
| 2009/0118365 A1 | 5/2009 | Benson, III et al. |
| 2012/0027723 A1 | 2/2012 | Picaud |

FOREIGN PATENT DOCUMENTS

| WO | WO-2005/027950 | 3/2005 |
| WO | WO-2009/004082 | 1/2009 |
| WO | WO-2010/089355 | 8/2010 |

OTHER PUBLICATIONS

Liu et al. International Scholarly Research Network, ISRN Ophthalmology, vol. 2012, Article ID 480212, pp. 1-9.*
Bansal, et al., "What is new in the management of age-related macular degeneration", Journal International Medical Sciences Academy, International Medical Sciences Academy, New Delhi, IN, vol. 23, No. 3, Sep. 1, 2010.

\* cited by examiner

*Primary Examiner* — James D Anderson
(74) *Attorney, Agent, or Firm* — Cesari and McKenna LLP (57) ABSTRACT

The present invention relates to combinations and methods for the treatment of macular degeneration disorders. More specifically, the present invention relates to novel combinatorial therapies of Age related Macular Degeneration based on baclofen and acamprosate combination.

10 Claims, 2 Drawing Sheets

BACLOFEN AND ACAMPROSATE BASED THERAPY OF MACULAR DEGENERATION DISORDERS

CROSS REFERENCE TO RELATED APPLICATIONS

This application is the National Stage of International Application No. PCT/EP2013/065209, filed on Jul. 18, 2013, which claims the benefit of U.S. Provisional Application No. 61/672,893, filed on Jul. 18, 2012. The contents of both applications are hereby incorporated by reference in their entirety.

FIELD OF THE INVENTION

The present invention relates to combinations and methods for the treatment of macular degeneration disorders. More specifically, the present invention relates to novel combinatorial therapy of AMD, based on baclofen and acamprosate combination.

BACKGROUND OF THE INVENTION

Age-related macular degeneration (AMD) is a leading cause of blindness worldwide, affecting ageing populations. It has been estimated that 80 million people will be affected by AMD by 2020. The prevalence is 10% in patients 66 to 74 years of age that increases to 30% in patients 75 to 85 years of age. AMD is a degenerative disease characterized by progressive impairment of the macula, located near to the center of retina. Macula is the most concentrated region in photoreceptors and is therefore involved in central vision and visual acuity. There are risk factors associated with AMD, older age being the major one. Others consist in ocular factors (darker iris pigmentation, previous cataract surgery, hyperopic refraction) or systemic factors (cigarette smoking, obesity, diet, race, retinal stress (sunlight exposure) and cardiovascular diseases). Several genetic loci have been associated with AMD, including elements of the complement system such as CFH, the ARMS2/HTRA1 locus, C2, CFB, C3 and CF1. Genes of the HDL cholesterol pathway (LIPC, CETP and possibly ABCA1 and LDL), the LDL pathway (possibly APOE), the extracellular matrix (COL10A1, COL8A1, TIMP3), Glial Fibrillary Acidic Protein (GFAP) and the angiogenesis pathway (VEGFA) have also been associated with AMD [1,2].

Etiology and pathogenesis of AMD remain unclear, even if many biological processes have been implicated in AMD pathogenesis such as senescence identified in the retinal pigment epithelium (RPE; the pigmented cell layer just outside the retina that nourishes retinal cells) with lipofuscin accumulation, choroidal ischemia, oxidative damage and inflammation. Attention has also recently been focused on the Vascular Endothelial Growth Factor (VEGF) due to its role as a therapeutic target. The first clinical and pathological manifestations of AMD are thickening and loss of normal architecture in the Bruch's membrane (the innermost layer of the choroid, the vascular layer involved in the supply of nutrients to the retina), lipofuscin accumulation in RPE and increased number of large drusen. Drusen are extracellular deposits that accumulate inside the Bruch's membrane and below the RPE. They are composed of cellular remnants and debris derived from degenerate RPE cells, and proteins such as glycoproteins, lipids, apoliproproteins B and E, factor X, amyloid P component, amyloid β, immunoglobulins and inflammation-related proteins (including proteins of the complement system such as C5 and C5b-9 terminal complexes), as well as complement regulators (vitronectin and clusterin). Their precise role in the pathogenesis of AMD remains unclear; but it has been a long time since they are recognized as AMD hallmark [1].

Presence of many soft drusen (large and poorly demarcated) in the macula characterizes early AMD, together with RPE pigmentation impairment. Early AMD is associated with an important risk of progression to late AMD, where visual impairment happens. Late AMD occurs in two different forms, the wet (⅓ of patients) and the dry forms (⅔ of patients). In the wet or neovascular AMD form, loss of vision is a consequence of abnormal blood vessel growth (choroidal neovascularization) in the capillaries layer of the choroid. This process ultimately leads to bleeding, protein leaking, and scarring from these blood vessels below the macula and finally causes irreversible damage to the photoreceptors and rapid vision loss if left untreated. The dry form, or geographic atrophy, is characterized by the cell loss of RPE that manifests by oval areas of hypopigmentation. This process leads to photoreceptors degeneration since RPE cells are involved in their sustaining Retina becomes thinner, resulting in a progressive impairment of vision [1].

Until recently, laser treatment (photocoagulation) was the only approved treatment of wet AMD. This technique aims at ablating new choroidal blood vessels associated with little damages to surrounding retinal tissue. The long-term severe visual loss is efficiently reduced, but there is no gain of vision, as well as a high recurrence rate (50%) and a 41% risk of developing an immediate moderate visual loss. Improvement occurred with the use of photosensitizing agents such as verteporfin delivered intravenously just before laser treatment that accumulate preferentially in neovascular membranes [3]. Despite encouraging results these therapeutic options are much less used because they target only end-stage of the disease and do not act on its progression.

Anti-VEGF drugs are now the standard of care of the choroidal neovascularization pathogenesis. There are actually several VEGF inhibitors marketed for this indication: pegaptanib, ranibizumab, aflibercept, in addition to bevacizumab commonly used as an alternative off-label treatment. Use of these treatments is associated with significant visual stabilization and improvement. There are however two major issues: the need for a rigorous monthly administration, increasing the risk of complications such as endophthalmitis and the long-term safety issue of VEGF inhibitors that may potently enter the systemic circulation after ocular injection, especially bevacizumab and ranibizumab, leading to higher risk of vascular events. Much effort has focused on improvement of anti-VEGF treatments protocols in order to reduce the frequency of injections. As an example, the combination of anti-VEGF therapies together with photodynamic therapy and corticosteroids have been proposed, but recent results report insignificant improvements [4,5].

There is currently no treatment that stops or even slows down progression of the dry AMD. Many strategies are being tested in clinical trials. They aim at targeting either retinal toxins or complement or trophic factor supplementation or oxidative stress or inflammation.

There are obvious unmet medical needs concerning AMD treatments since non-fully satisfying treatments are available.

SUMMARY OF INVENTION

It is an object of this invention to provide a treatment for macular degeneration disorders. More precisely, this invention relates to compositions and methods for treating macular degeneration disorders based on the use of baclofen and acamprosate.

As shown in this application, the methods and compositions of the invention allow an unexpected and remarkable improvement in physiological ailments of the eyeball that are implicated in the etiology of several degenerative disorders of the macula. In particular, the inventors have found that baclofen and acamprosate based compositions are efficient against angiogenic injuries of the retina and against retina degeneration.

Moreover baclofen and acamprosate are effective in lowering oxidative stress and improving mitochondrial dysfunction and retinal stress observed in AMD.

An object of this invention thus relates to a composition comprising baclofen and acamprosate for use in treating, preventing, inhibiting or stopping the progression of a macular degeneration disorder and, more particularly, of dry or wet Age-related Macular Degeneration (AMD), Stargardt disease, early or adult onset vitelliform macular dystrophies or diabetic retinopathy.

An object of this invention relates to baclofen for use in combination with acamprosate in treating, preventing, inhibiting or stopping the progression of a macular degeneration disorder and, more particularly, of dry or wet Age-related Macular Degeneration (AMD), Stargardt disease, early or adult onset vitelliform macular dystrophies or diabetic retinopathy.

Another object of this invention is the use of a composition comprising baclofen and acamprosate to prevent progression toward macular degeneration in a subject diagnosed as bearing drusen or retinal pigmentory changes or experiencing retinal degeneration or abnormal ocular angiogenesis.

The invention also relates to any pharmaceutical composition per se comprising a combination of baclofen and acamprosate as defined above.

The compositions of the invention typically further comprise one or several pharmaceutically acceptable excipients or carriers. Also, the compounds as used in the present invention may be in the form of salts, hydrates, esters, ethers, acids, amides, racemates, or isomers. They may also be in the form of sustained-release formulations. Prodrugs or derivatives of the compounds may be used as well. In a preferred embodiment, a calcium acamprosate is used.

As it will be disclosed in this application, compounds in the compositions of the invention may be formulated or administered together, separately or sequentially. Said combinations may also be formulated or administered together, separately or sequentially.

Another object of this invention relates to method for treating, preventing, inhibiting or stopping the progression of a macular degeneration disorder in a subject in need thereof, the method comprising administering to the subject an effective amount of baclofen and acamprosate.

Another object of this invention relates to the use of baclofen and acamprosate for the manufacture of a medicament for treating, preventing, inhibiting or stopping the progression of a macular degeneration disorder.

The invention may be used in any mammal, preferably human beings.

DETAILED DESCRIPTION OF THE INVENTION

The present invention provides new methods and compositions for the treatment of macular degeneration disorders. The invention discloses novel drug compositions which allow an effective correction of such diseases and may be used in any mammalian subject.

The invention is suited for macular degeneration disorders wherein retinal pigment epithelium and finally retina neuronal cells are impaired. Specific examples of such disorders include Age-related Macular Degeneration (AMD), inherited macular degeneration, or diabetic retinopathy.

Age-related Macular Degeneration (AMD) refers to dry or wet AMD, wherein the main risk factor is ageing.

Inherited macular degeneration refers to macular degeneration syndromes with an earlier onset as Stargardt disease or early and adult onset vitelliform macular dystrophies.

The invention is particularly suited for treating AMD.

As used herein, "treatment" includes the therapy, prevention, prophylaxis, retardation or reduction of symptoms provoked by or of the causes of the above diseases or disorders. The term treatment includes in particular the control of disease progression and associated symptoms. The term treatment particularly includes a protection against angiogenic injuries, or a reduction or retardation of said injuries and/or an inhibition of retinal degeneration and RPE atrophy, or a reduction or retardation of said degeneration and atrophy, in the treated subjects. The term treatment also includes the stop or retardation of the disease progression from the early to the late forms (i.e. wet or dry) of AMD.

Within the context of this invention, the designation of a specific drug or compound is meant to include not only the specifically named molecule, but also any pharmaceutically acceptable salt, hydrate, derivative, isomer, racemate, conjugate, prodrug or derivative thereof of any chemical purity.

The term "combination" or "combinatorial treating/therapy" designates a treatment wherein at least baclofen and acamprosate are co-administered to a subject to cause a biological effect. In a combined therapy according to this invention, the at least two drugs may be administered together or separately, at the same time or sequentially. Also, the at least baclofen and acamprosate may be administered through different routes and protocols. As a result, although they may be formulated together, the drugs of a combination may also be formulated separately.

The term "prodrug" as used herein refers to any functional derivatives (or precursors) of a compound of the present invention, which, when administered to a biological system, generates said compound as a result of e.g., spontaneous chemical reaction(s), enzyme catalysed chemical reaction(s), and/or metabolic chemical reaction(s). Prodrugs are usually inactive or less active than the resulting drug and can be used, for example, to improve the physicochemical properties of the drug, to target the drug to a specific tissue, to improve the pharmacokinetic and pharmacodynamic properties of the drug and/or to reduce undesirable side effects. Prodrugs typically have the structure X-drug wherein X is an inert carrier moiety and drug is the active compound, wherein the prodrug is less active than the drug and the drug is released from the carrier in vivo.

Some of the common functional groups that are amenable to prodrug design include, but are not limited to, carboxylic, hydroxyl, amine, phosphate/phosphonate and carbonyl groups. Prodrugs typically produced via the modification of these groups include, but are not limited to, esters, carbonates, carbamates, amides and phosphates. Specific technical guidance for the selection of suitable prodrugs is general common knowledge [6-10]. Furthermore, the preparation of prodrugs may be performed by conventional methods known by those skilled in the art. Methods which can be used to synthesize other prodrugs are described in numerous reviews on the subject [7,11-17]. For example, Arbaclofen Placarbil is a well-known prodrug of baclofen [18,19] which is listed in ChemID plus Advance database (website: chem.sis.nlm.nih.gov/chemidplus/).

The term "derivative" of a compound includes any molecule that is functionally and/or structurally related to said compound, such as an acid, amide, ester, ether, acetylated variant, hydroxylated variant, or an alkylated (C1-C6) variant of such a compound. The term derivative also includes structurally related compound having lost one or more substituent as listed above. For example, Homotaurine is a deacetylated derivative of acamprosate. Preferred derivatives of a compound are molecules having a substantial degree of similarity to said compound, as determined by known methods. Similar compounds along with their index of similarity to a parent molecule can be found in numerous databases such as PubChem (http://pubchem.ncbi.nlm.nih.gov/search/) or DrugBank (http://www.drugbank.ca/). In a more preferred embodiment, derivatives should have a Tanimoto similarity index greater than 0.4, preferably greater than 0.5, more preferably greater than 0.6, even more preferably greater than 0.7 with a parent drug. The Tanimoto similarity index is widely used to measure the degree of structural similarity between two molecules. Tanimoto similarity index can be computed by software such as the Small Molecule Subgraph Detector [20,21] available online (http://www.ebi.ac.uk/thornton-srv/software/SMSD/). Preferred derivatives should be both structurally and functionally related to a parent compound, i.e., they should also retain at least part of the activity of the parent drug, more preferably they should have a protective activity against angiogenic injuries of the retina or should inhibit retina degeneration.

The term derivatives also include metabolites of a drug, e.g., a molecule which results from the (biochemical) modification(s) or processing of said drug after administration to an organism, usually through specialized enzymatic systems, and which displays or retains a biological activity of the drug. Metabolites have been disclosed as being responsible for much of the therapeutic action of the parent drug. In a specific embodiment, a "metabolite" as used herein designates a modified or processed drug that retains at least part of the activity of the parent drug, preferably that has a protective activity against angiogenic injuries of the retina or that inhibit retina degeneration.

The term "salt" refers to a pharmaceutically acceptable and relatively non-toxic, inorganic or organic acid addition salt of a compound of the present invention. Pharmaceutical salt formation consists in pairing an acidic, basic or zwitterionic drug molecule with a counterion to create a salt version of the drug. A wide variety of chemical species can be used in neutralization reaction. Pharmaceutically acceptable salts of the invention thus include those obtained by reacting the main compound, functioning as a base, with an inorganic or organic acid to form a salt, for example, salts of acetic acid, nitric acid, tartric acid, hydrochloric acid, sulfuric acid, phosphoric acid, methane sulfonic acid, camphor sulfonic acid, oxalic acid, maleic acid, succinic acid or citric acid. Pharmaceutically acceptable salts of the invention also include those in which the main compound functions as an acid and is reacted with an appropriate base to form, e.g., sodium, potassium, calcium, magnesium, ammonium, or choline salts. Though most of salts of a given active principle are bioequivalents, some may have, among others, increased solubility or bioavailability properties. Salt selection is now a common standard operation in the process of drug development as taught by H. Stahl and C. G Wermuth in their handbook [22].

In a preferred embodiment, the designation of a compound is meant to designate the compound per se, as well as any pharmaceutically acceptable salt, hydrate, isomer, racemate, ester or ether thereof.

In a more preferred embodiment, the designation of a compound is meant to designate the compound as specifically designated per se, as well as any pharmaceutically acceptable salt thereof.

In a particular embodiment, a sustained-release formulation of the compound is used.

As discussed above, the invention relates to novel approaches for treating macular degeneration disorders such as wet or dry AMD, Stargardt disease or early and adult onset vitelliform macular dystrophies or diabetic retinopathy. As disclosed in this application, the methods and compositions of the invention exert a strong unexpected effect on biological processes which lead to macular degeneration. Furthermore, although baclofen and acamprosate are efficient alone for use in the treatment of AMD, Stargardt disease, early or adult onset vitelliform macular dystrophies and diabetic retinopathy, the invention discloses more specifically compositions comprising baclofen in combination with acamprosate, which provide a significant effect in vivo on macular disorders.

Indeed, the invention shows, in the experimental part, that combination therapies comprising baclofen and acamprosate can substantially improve the condition of patients afflicted with macular degeneration disorders. In particular, as shown in the experimental section, baclofen and acamprosate combinations have a strong, unexpected effect on leakage observed in induced choroidal angiogenesis and on induced retinal degeneration. More generally, combinations of the invention are also found efficient in reducing oxidative stress and mitochondrial dysfunction which are hallmarks of RPE and retinal degeneration and, hence, components of the pathogenesis of AMD.

The present invention therefore provides a novel therapy of macular degeneration disorders based on baclofen and acamprosate. More particularly, the present invention proposes a novel therapy of AMD, wet or dry, and of Stargardt disease, early and adult onset vitelliform macular dystrophies or diabetic retinopathy, based on baclofen and acamprosate combinations.

In this regard, the invention thus relates to a composition comprising baclofen and acamprosate for use in the treatment of wet or dry AMD.

Another object of the invention relates to baclofen in combination with acamprosate for use in the treatment of wet or dry AMD.

In a further embodiment the invention relates to a composition comprising baclofen and acamprosate for use in a treatment of other macular degeneration disorders as Stargardt disease or early and adult onset vitelliform macular dystrophies or diabetic retinopathy.

In another embodiment, the invention relates to the use of baclofen and acamprosate for the manufacture of a medicament for the treatment of wet or dry AMD, Stargardt disease or early and adult onset vitelliform macular dystrophies or diabetic retinopathy.

Illustrative CAS numbers for baclofen and acamprosate are provided in Table 1 below. Table 1 cites also, in a non-limitative way, common salts, racemates, prodrugs, metabolites or derivatives for these compounds used in the compositions of the invention.

TABLE 1

| Drug | CAS Numbers | Class or Tanimoto similarity index |
|---|---|---|
| Acamprosate and related compounds | | |
| Acamprosate | 77337-76-9; 77337-73-6 | NA |
| Homotaurine | 3687-18-1 | 0.73 |
| Ethyl Dimethyl Ammonio Propane Sulfonate | / | 0.77 |
| Taurine | 107-35-7 | 0.5 |
| Baclofen and related compounds | | |
| Baclofen | 1134-47-0; 66514-99-6; 69308-37-8; 70206-22-3; 63701-56-4; 63701-55-3 | NA |
| 3-(p-chlorophenyl)-4-hydroxybutyric acid | / | Metabolite |
| Arbaclofen placarbil | 847353-30-4 | Prodrug |

Specific examples for baclofen prodrugs are given in Hanafi et al., 2011 [23] who had shown baclofen esters and ester carbamates as of particular interest for CNS targeting, and, consequently might be considered of interest when talking of retinal cells targeting. Hence such prodrugs are particularly suitable for compositions of this invention. Arbaclofen placarbil as mentioned before is also a well-known prodrug and may thus be used instead of baclofen in compositions of the invention. Other prodrugs for baclofen can be found in the following patent applications: WO2010102071, US2009197958, WO2009096985, WO2009061934, WO2008086492, US2009216037, WO2005066122, US2011021571, WO2003077902, WO2010120370.

Useful prodrugs for acamprosate such as pantoic acid ester neopentyl sulfonyl esters, neopentyl sulfonyl esters prodrugs or masked carboxylate neopentyl sulfonyl ester prodrugs of acamprosate are notably listed in WO2009033069, WO2009033061, WO2009033054 WO2009052191, WO2009033079, US 2009/0099253, US 2009/0069419, US 2009/0082464, US 2009/0082440, and US 2009/0076147.

In a particular embodiment, the invention relates to the use of baclofen and acamprosate combination for treating, preventing, inhibiting or stopping the progression of dry or wet AMD in a subject in need thereof.

Another object of the invention is the use of this combination in a subject in whom drusen or retinal pigmentory changes have been detected in the macula in order to prevent, to slow or to stop the development of a macular degeneration disorder. Indeed, the presence of soft drusen in the macula or RPE pigment disruption characterizes early AMD but also diabetic retinopathy in which the angiogenic disruption of RPE leading to the angiogenic destruction retina is observed.

Another object of the invention relates to the use of said combination for treating, preventing, inhibiting or stopping the progression diabetic retinopathy in a subject in need thereof.

As disclosed in the examples, compositions therapies of the invention exert a beneficial effect in protecting cells from the inter related oxydative stress and mitochondrial impairment, that are particularly important in the aetiology of AMD. Moreover composition therapies using at least baclofen and acamprosate have a strong unexpected effect, on biological processes implied in wet or dry AMD pathogenesis; they are efficient in lowering retinal degeneration and choroidal angiogenesis injuries. These combinations therefore represent novel approaches for treating macular degeneration disorders, such as dry or wet AMD, in human subjects.

In a combination therapy of this invention, the compounds or drugs may be formulated together or separately, and administered together, separately or sequentially.

A further object of this invention resides in the use of a composition as defined above for the manufacture of a medicament for treating, preventing, inhibiting or stopping the progression of a macular degeneration disorder such as dry and wet AMD, Stargardt disease or early and adult onset vitelliform macular dystrophies or diabetic retinopathy.

The invention further provides a method for treating, preventing, inhibiting or stopping the progression of a macular degeneration disorder such as dry and wet AMD, Stargardt disease or early and adult onset vitelliform macular dystrophies or diabetic retinopathy comprising administering to a subject in need thereof an effective amount of a composition as disclosed above.

A further object of the invention is a method of treating, preventing, inhibiting or stopping the progression of a macular degeneration disorder such as dry and wet AMD, Stargardt disease or early and adult onset vitelliform macular dystrophies or diabetic retinopathy, the method comprising simultaneously, separately or sequentially administering to a subject in need thereof an effective amount of a composition as disclosed above.

In a preferred embodiment, the invention relates to a method of treating, preventing, inhibiting or stopping the progression of a macular degeneration disorder such as dry and wet AMD, Stargardt disease or early and adult onset vitelliform macular dystrophies or diabetic retinopathy in a subject in need thereof, comprising administering simultaneously, separately or sequentially to the subject an effective amount of baclofen and acamprosate.

The compositions of the invention typically comprise one or several pharmaceutically acceptable carriers or excipients. Also, for use in the present invention, the drugs or compounds are usually mixed with pharmaceutically acceptable excipients or carriers.

In this regard, a further object of this invention is a method of preparing a pharmaceutical composition, the method comprising mixing the above compounds in an appropriate excipient or carrier.

In a particular embodiment, the method comprises mixing baclofen and acamprosate in an appropriate excipient or carrier.

According to preferred embodiments of the invention, as indicated above, the compounds are used as such or in the form of a pharmaceutically acceptable salt, prodrug, derivative, or sustained release formulation thereof.

Baclofen and acamprosate combination may be used alone or may be further combined with additional compounds.

For instance, although very effective in vitro and in vivo, depending on the subject or specific condition, the combination therapy of the invention may further be used in conjunction or association or combination with additional drugs or treatments beneficial to the treated macular degeneration condition in the subjects.

Other therapies used in conjunction with drug(s) or drug(s) combination(s) according to the present invention, may comprise one or more drug(s) that ameliorate symptoms of AMD, dry or wet. Thereby, illustrative therapies which can be used with combinations of the invention are pegaptanib, ranibizumab, aflibercept, or bevacizumab. Other additional therapies that could be contemplated are for example nutritional complementation with anti-oxidants and/or zinc intake.

In a particular embodiment, the drug(s) or compositions according to the present invention may be further used in patients planned to be subjected or having been subjected to laser treatment of drusen or to photodynamic therapy using, optionally, verteporfin or other anti-angiogenic drug(s).

Therapy according to the invention may be provided at home, the doctor's office, a clinic, a hospital's outpatient department, or a hospital, so that the doctor can observe the therapy's effects closely and make any adjustments that are needed.

The duration of the therapy depends on the stage of the disease being treated, age and condition of the patient, and how the patient responds to the treatment. The dosage, frequency and mode of administration of each component of the combination can be controlled independently. For example, one drug may be administered orally while the second drug may be administered ocularly or intraocularly. Combination therapy may be given in on-and-off cycles that include rest periods so that the patient's body has a chance to recovery from any as yet unforeseen side-effects. The drugs may also be formulated together such that one administration delivers all drugs.

The administration of each drug of the combination may be by any suitable means that results in a concentration of the drug that, combined with the other component, is able to ameliorate the patient condition or efficiently treat the disease or disorder.

While it is possible for the drugs or the drug combinations to be administered as the pure chemical, it is preferable to present them as a pharmaceutical composition, also referred to, in this context, as pharmaceutical formulation. Possible compositions include those suitable for oral, topical (ocular instillations), or parenteral (intraocular injection) administration.

More commonly these pharmaceutical formulations are prescribed to the patient in "patient packs" containing a number dosing units or other means for administration of metered unit doses for use during a distinct treatment period in a single package, usually a blister pack. Patient packs have an advantage over traditional prescriptions, where a pharmacist divides a patient's supply of a pharmaceutical from a bulk supply, in that the patient always has access to the package insert contained in the patient pack, normally missing in traditional prescriptions. The inclusion of a package insert has been shown to improve patient compliance with the physician's instructions. Thus, the invention further includes a pharmaceutical formulation, as herein before described, in combination with packaging material suitable for said formulations. In such a patient pack the intended use of a formulation for the combination treatment can be inferred by instructions, facilities, provisions, adaptations and/or other means to help using the formulation most suitably for the treatment. Such measures make a patient pack specifically suitable for and adapted for use for treatment with the combination of the present invention.

The drugs may be contained, in any appropriate amount, in any suitable carrier substance. Drugs may be present in an amount of up to 99% by weight of the total weight of the composition. The composition may be provided in a dosage form that is suitable for oral, parenteral (e.g. intraocularly), or ocular administration route. Thus, the composition may be in the form of, e.g. suspensions, emulsions, solutions, gels including hydrogels, creams, drenches, osmotic delivery devices, injectables, implants, sprays, or aerosols.

The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

Pharmaceutical compositions according to the invention may be formulated to release the active drug substantially immediately upon administration or at any predetermined time or time period after administration.

The controlled release formulations include (i) formulations that create a substantially constant concentration of the drug within the body over an extended period of time; (ii) formulations that after a predetermined lag time create a substantially constant concentration of the drug within the body over an extended period of time; (iii) formulations that sustain drug action during a predetermined time period by maintaining a relatively, constant, effective drug level in the body with concomitant minimization of undesirable side effects associated with fluctuations in the plasma level of the active drug substance; (iv) formulations that localize drug action by, e.g., spatial placement of a controlled release composition adjacent to or in the diseased tissue or organ; and (v) formulations that target drug action by using carriers or chemical derivatives to deliver the drug to a particular target cell type.

Administration of drugs in the form of a controlled release formulation is especially preferred in cases in which the drug has (i) a narrow therapeutic index (i.e., the difference between the concentration leading to harmful side effects or toxic reactions and the concentration leading to a therapeutic effect is small; in general, the therapeutic index, TI, is defined as the ratio of median lethal dose (LD50) to median effective dose (ED50)); (ii) a narrow absorption window in the gastro-intestinal tract; or (iii) a very short biological half-life so that frequent dosing during a day is required in order to sustain the plasma level at a therapeutic level.

Any of a number of strategies can be pursued in order to obtain controlled release in which the rate of release outweighs the rate of metabolism of the drug in question. Controlled release may be obtained by appropriate selection of various formulation parameters and ingredients, including, e.g., various types of controlled release compositions and coatings. Thus, the drug is formulated with appropriate excipients into a pharmaceutical composition that, upon administration, releases the drug in a controlled manner (oil solutions, suspensions, emulsions, microcapsules, microspheres, nanoparticles, and liposomes).

Solid Dosage Forms for Oral Use

Formulations for oral use include tablets containing the composition of the invention in a mixture with non-toxic pharmaceutically acceptable excipients. These excipients may be, for example, inert diluents or fillers (e.g., sucrose, microcrystalline cellulose, starches including potato starch, calcium carbonate, sodium chloride, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., acacia, alginic acid, sodium alginate, gelatin, starch, pregelatinized starch, microcrystalline cellulose, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., stearic acid, silicas, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby providing a sustained action over a longer period. The coating may be adapted to release the active drug substance in a predetermined pattern (e.g., in order to achieve a controlled release formulation) or it may be adapted not to release the active drug substance until after passage of the stomach (enteric coating). The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). A time delay material such as, e.g., glyceryl monostearate or glyceryl distearate may be employed.

The solid tablet compositions may include a coating adapted to protect the composition from unwanted chemical changes, (e.g., chemical degradation prior to the release of the active drug substance). The coating may be applied on the solid dosage form in a similar manner as that described in Encyclopedia of Pharmaceutical Technology.

Drugs may be mixed together in the tablet, or may be partitioned. For example, a first drug is contained on the inside of the tablet, and a second drug is on the outside, such that a substantial portion of the second drug is released prior to the release of the first drug.

Formulations for oral use may also be presented as chewable tablets, or as hard gelatin capsules wherein the active ingredient is mixed with an inert solid diluent (e.g., potato starch, microcrystalline cellulose, calcium carbonate, calcium phosphate or kaolin), or as soft gelatin capsules wherein the active ingredient is mixed with water or an oil medium, for example, liquid paraffin, or olive oil. Powders and granulates may be prepared using the ingredients mentioned above under tablets and capsules in a conventional manner.

Controlled release compositions for oral use may, e.g., be constructed to release the active drug by controlling the dissolution and/or the diffusion of the active drug substance.

Dissolution or diffusion controlled release can be achieved by appropriate coating of a tablet, capsule, pellet, or granulate formulation of drugs, or by incorporating the drug into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

A controlled release composition containing one or more of the drugs of the claimed combinations may also be in the form of a buoyant tablet or capsule (i.e., a tablet or capsule that, upon oral administration, floats on top of the gastric content for a certain period of time). A buoyant tablet formulation of the drug(s) can be prepared by granulating a mixture of the drug(s) with excipients and 20-75% w/w of hydrocolloids, such as hydroxyethylcellulose, hydroxypropylcellulose, or hydroxypropylmethylcellulose. The obtained granules can then be compressed into tablets. On contact with the gastric juice, the tablet forms a substantially water-impermeable gel barrier around its surface. This gel barrier takes part in maintaining a density of less than one, thereby allowing the tablet to remain buoyant in the gastric juice.

Liquids for Oral Administration

Powders, dispersible powders, or granules suitable for preparation of an aqueous suspension by addition of water are convenient dosage forms for oral administration. Formulation as a suspension provides the active ingredient in a mixture with a dispersing or wetting agent, suspending agent, and one or more preservatives. Suitable suspending agents are, for example, sodium carboxymethylcellulose, methylcellulose, sodium alginate, and the like.

Parenteral Compositions

The pharmaceutical composition may be administered parenterally by intraocular injection in dosage forms, formulations, or via suitable delivery devices or containing conventional, non-toxic pharmaceutically acceptable carriers and adjuvants. The formulation and preparation of such compositions are well known to those skilled in the art of pharmaceutical formulation.

Compositions for parenteral use may be provided in unit dosage forms (e.g., in single-dose ampoules), or in vials containing several doses and in which a suitable preservative may be added (see below). The composition may be in form of a solution, a suspension, an emulsion, an infusion device, or a delivery device for implantation or it may be presented as a dry powder to be reconstituted with water or another suitable vehicle before use. Apart from the active drug(s), the composition may include suitable parenterally acceptable carriers and/or excipients. The active drug(s) may be incorporated into microspheres, microcapsules, nanoparticles, liposomes, or the like for controlled release. The composition may include suspending, solubilizing, stabilizing, pH-adjusting agents, and/or dispersing agents.

The pharmaceutical compositions according to the invention may be in the form suitable for sterile injection. To prepare such a composition, the suitable active drug(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution. The aqueous formulation may also contain one or more preservatives (e.g., methyl, ethyl or n-propyl p-hydroxybenzoate). In cases where one of the drugs is only sparingly or slightly soluble in water, a dissolution enhancing or solubilizing agent can be added, or the solvent may include 10-60% w/w of propylene glycol or the like.

Controlled release parenteral compositions may be in form of aqueous suspensions, microspheres, microcapsules, magnetic microspheres, oil solutions, oil suspensions, or emulsions. Alternatively, the active drug(s) may be incorporated in biocompatible carriers, liposomes, nanoparticles, implants, or infusion devices. Materials for use in the preparation of microspheres and/or microcapsules are, e.g., biodegradable/bioerodible polymers such as polygalactin, poly-(isobutyl cyanoacrylate), poly(2-hydroxyethyl-L-glutamine). Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly(glycolic acid) or poly(ortho esters)).

Ocular Instillations

The pharmaceutical compositions may also be administered topically through eyedrop instillations, in dosage forms or formulations containing conventionally non-toxic pharmaceutical acceptable carriers and excipients including microspheres and liposomes. The formulations include lotions, liniments, gels, hydrogels, solutions, suspensions, sprays, and other kinds of drug delivery systems. The pharmaceutically acceptable carriers or excipients may include emulsifying agents, antioxidants, buffering agents, preservatives, humectants, penetration enhancers, chelating agents, gel-forming agents, ointment bases, perfumes, and skin protective agents.

Dosages and Duration of the Treatment

It will be appreciated that the drugs of the combination may be administered concomitantly, either in the same or different pharmaceutical formulation or sequentially. If there is sequential administration, the delay in administering the second (or additional) active ingredient should not be such as to lose the benefit of the efficacious effect of the combination of the active ingredients. A minimum requirement for a combination according to this description is that the combination should be intended for combined use with the benefit of the efficacious effect of the combination of the active ingredients. The intended use of a combination can be inferred by facilities, provisions, adaptations and/or other means to help using the combination according to the invention.

Therapeutically effective amounts of the drugs in a combination of this invention include, e.g., amounts that are effective for reducing AMD symptoms, halting or slowing the progression of the disease once it has become clinically manifest, or prevention or reduction of the risk of developing the late form of the disease.

Although the active drugs of the present invention may be administered in divided doses, for example two or three times daily, a single daily dose of each drug in the combination is preferred, with a single daily dose of all drugs in a single pharmaceutical composition being most preferred.

Administration can be one to several times daily for several days to several years, and may even be for the life of the patient. Chronic or at least periodically repeated long-term administration is indicated in most cases.

The term "unit dosage form" refers to physically discrete units (such as capsules or loaded syringe cylinders) suitable as unitary dosages for human subjects, each unit containing a predetermined quantity of active material or materials calculated to produce the desired therapeutic effect, in association with the required pharmaceutical carrier.

The amount of each drug in a preferred unit dosage composition depends upon several factors including the administration method, the body weight and the age of the patient, the stage of the disease, the risk of potential side effects considering the general health status of the person to be treated. Additionally, pharmacogenomic (the effect of genotype on the pharmacokinetic, pharmacodynamic or efficacy profile of a therapeutic) information about a particular patient may affect the dosage used.

Except when responding to especially impairing cases, where higher dosages may be required, the preferred dosage of each drug in the combination will usually lie within the range of doses not above the dosage usually prescribed for long-term maintenance treatment or proven to be safe in phase 3 clinical studies.

One remarkable advantage of the invention is that each compound may be used at low doses in a combination therapy, while producing, in combination, a synergistic effect resulting in a substantial clinical benefit to the patient. The combination therapy may indeed be effective at doses where the compounds have individually low or no effect. Accordingly, a particular advantage of the invention lies in the ability to use sub-optimal doses of each compound, i.e., doses which are lower than therapeutic doses usually prescribed, preferably ½ of therapeutic doses, more preferably ⅓, ¼, ⅕, or even more preferably ⅒ of therapeutic doses. In particular examples, doses as low as ¹⁄₂₀, ¹⁄₃₀, ¹⁄₅₀, ¹⁄₁₀₀, or even lower, of therapeutic doses are used.

At such sub-therapeutic dosages, the compounds would exhibit no side effect, while the combination(s) according to the invention are fully effective in treating AMD or Stargardt disease, early or adult onset vitelliform macular dystrophies or diabetic retinopathy.

A preferred dosage corresponds to amounts from 1% up to 50% of those usually prescribed for long-term maintenance treatment.

The most preferred dosage may correspond to amounts from 1% up to 10% of those usually prescribed for long-term maintenance treatment.

Specific examples of oral dosages of drugs for use according to the invention are provided below:

Acamprosate between 1 and 1000 mg/day, preferably less than 500 mg per day, more preferably less than 100 mg/day, even more preferably less than 10 mg/day, such dosages being particularly suitable for oral administration.

Baclofen between 0.01 and 150 mg per day, preferably less than 100 mg per day, more preferably less than 75 mg/day, even more preferably less than 50 mg/day, such dosages being particularly suitable for oral administration.

When the composition comprises, as active ingredients, only baclofen and acamprosate, these two compounds may be used in different ratios, e.g., at a weight ratio baclofen/acamprosate comprised between 0.05 to 1000 (W:W), preferably between 0.05 to 500 (W:W), more preferably between 0.05 to 100 (W:W), more preferably between 0.05 to 50 (W:W).

It will be understood that the amount of the drug actually administered will be determined by a physician, in the light of the relevant circumstances including the condition or conditions to be treated, the exact composition to be administered, the age, weight, and response of the individual patient, the severity of the patient's symptoms, and the chosen route of administration. Therefore, the above dosage ranges are intended to provide general guidance and support for the teachings herein, but are not intended to limit the scope of the invention.

The following examples are given for purposes of illustration and not by way of limitation.

EXAMPLES

I. Effect of Combinations of the Invention on Oxidative Stress

Oxidative stress has been shown as being strongly associated with AMD pathogenesis. This phenomenon is suspected to be the cause of mitochondrial dysfunction which in turn generates reactive oxygen species. Both RPE cells and retinal nervous cells are particularly susceptible to oxidative insults [24,25]. In the experiments shown below, inventors have found that compositions comprising baclofen and acamprosate are particularly efficient in lowering oxidative stress and mitochondrial dysfunction induced by 6-hydroxydopamine (6-OHDA) or amyloid β, this latter being found as a component of drusen.

a. Baclofen and acamprosate combinations are efficient in protecting neuronal cells from chemically induced mitochondrial poisoning by 6OHDA.

6-OHDA is a neurotoxic drug which destroys neurons by generating reactive oxygen species and inducing mitochondrial death in the cells. Due to its structural similarity with dopamine, 6OHDA is thought to enter specifically within dopaminergic neurons via specific dopamine active transporters. Notwithstanding, results below do show that combinations of the invention are efficient in protecting nervous cells from oxidative stress.

Culture of Mesencephalic Dopaminergic Neurons

Rat dopaminergic neurons were cultured as described by Schinelli et al. (1988) [26]. Pregnant female rats of 15 days gestation were killed by cervical dislocation (Rats Wistar; Janvier) and the foetuses removed from the uterus. The embryonic midbrains were removed and placed in ice-cold medium of Leibovitz (L15; PanBiotech) containing 2% of Penicillin-Streptomycin (PS; PanBiotech) and 1% of bovine serum albumin (BSA; PanBiotech). Only the ventral portions of the mesencephalic flexure were used for the cell preparations as this is the region of the developing brain rich in dopaminergic neurons. The midbrains were dissociated by trypsinisation for 20 min at 37° C. (Trypsin EDTA 1×; PanBiotech). The reaction is stopped by the addition of Dulbecco's modified Eagle's medium (DMEM; PanBiotech) containing DNAase I grade II (0.1 mg/ml; PanBiotech) and 10% of foetal calf serum (FCS; Invitrogen). Cells were then mechanically dissociated by 3 passages through a 10 ml pipette and centrifuged at 180×g for 10 min at +4° C. on a layer of BSA (3.5%) in L15 medium. The supernatant was discarded and the cells of pellet were re-suspended in a defined culture medium consisting of Neurobasal (Invitrogen) supplemented with B27 (2%; Invitrogen), L-glutamine (2 mM; PanBiotech) and 2% of PS solution and 10 ng/ml of Brain-derived neurotrophic factor (BDNF, PanBiotech) and 1 ng/ml of Glial-Derived Neurotrophic Factor (GDNF, PanBiotech). Viable cells were counted in a Neubauer cytometer using the trypan blue exclusion test. The cells were seeded at a density of 40 000 cells/well in 96 well-plates (pre-coated with poly-L-lysine (Greiner)) and are cultured at 37° C. in a humidified air (95%)/CO2 (5%) atmosphere. Half of the medium was changed every 2 days with fresh medium. Five to six percents of the neuronal cell population were dopaminergic neurons.

6-OHDA and Tests Compounds Exposure

On day 6 of culture, the medium was removed and fresh medium was added, without or with 6OHDA at the following concentrations: 20 µM during 48 hours diluted in control medium. Test compounds were pre-incubated for 1 h before the 6-OHDA application during 48 hours.

End Point Evaluation: Measure of Total Number of TH Positive Neurons

After 48 hours of intoxication with 6OHDA, cells were fixed by a solution of 4% paraformaldehyde (Sigma) in PBS, pH=7.3 for 20 min at room temperature. The cells were washed again twice in PBS, and then permeabilized and non-specific sites were blocked with a solution of PBS containing 0.1% of saponin (Sigma) and 1% FCS for 15 min at room temperature. Then, cells were incubated with Monoclonal Anti-Tyrosine Hydroxylase antibody produced in mouse (TH, Sigma) at dilution of 1/1000 in PBS containing 1% FCS, 0.1% saponin, for 2 h at room temperature. These antibodies were revealed with Alexa Fluor 488 goat anti-mouse IgG (Molecular Probes) at the dilution 1/800 in PBS containing 1% FCS, 0.1% saponin, for 1 h at room temperature.

For each condition, 2×10 pictures (representing ~80% of total well area) per well were taken using InCell Analyzer™ 1000 (GE Healthcare) with 10× magnification. All images were taken in the same conditions. Analysis of the number of TH positive neurons were done using Developer software (GE Healthcare).

Data are expressed in percentage of control conditions (no intoxication, no 6OHDA=100%) in order to express the 6OHDA injury. All values are expressed as mean+/−SEM (s.e. mean) of the 3 cultures (n=6 wells per condition per culture). Statistical analyses consist in an ANOVA followed by the Dunnett's and PLSD Fisher's tests when it was allowed using Statview software version 5.0.

Results

Results are summarized in table 2. A neuroprotective effect is observed for compounds and combinations of the invention in TH neurons survival test after 48 h 6-OHDA injury on dopaminergic neurons.

TABLE 2

| | In vitro | | | In vivo | | |
| | | | | Retinal degeneration | | |
| | 6OHDA resistance | MetO level | CytC level | Neovascular lesions | thickness of ONL | a-wave amplitude |
|---|---|---|---|---|---|---|
| Baclofen | improvement | – | – | na | na | na |
| Acamprosate | improvement | – | – | na | na | na |
| Baclofen and acamprosate | improvement | -- | -- | decrease | increase | increase |

Figure 1:
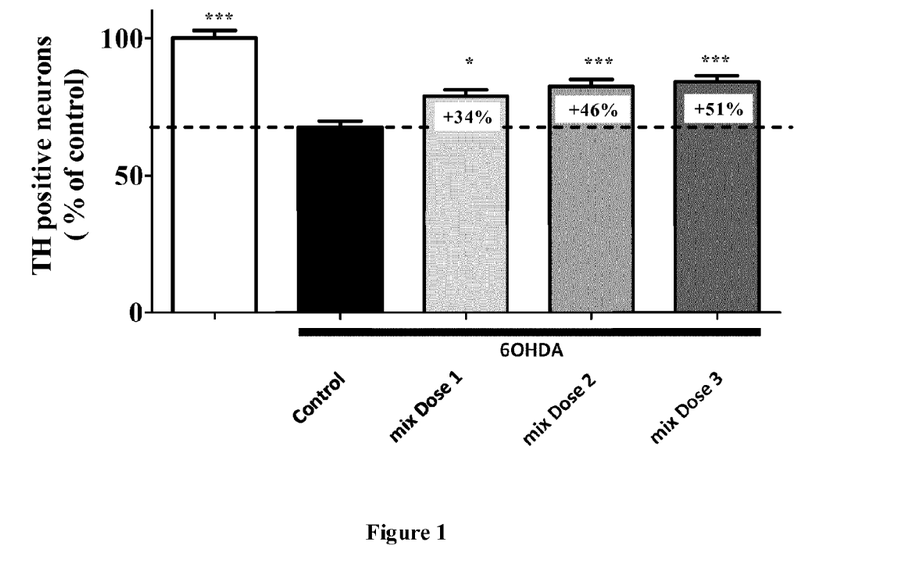
FIG. 1: Effect of baclofen and acamprosate combination therapy against 6OHDA induced oxidative stress. Baclofen and acamprosate therapy is efficient in protecting neuronal cells. The protection increases correlatively with concentration of mixes. A significant protective effect is observed with an increase in TH neurons survival by 34% with dose 1 (16 nM and 64 pM respectively), by 46% with dose 2 (80 nM and 144 pM) and by 51% with dose 3 (400 nM and 1600 pM) (***p<0.0001; *p<0.001: significantly different from 6OHDA intoxicated cells (ANOVA+Dunnett test))

\* ONL retinal outer nuclear layer;
na: not available;
– and -- intensity of lowering effect of compositions A 48 h 6-OHDA (20 µM) incubation with mesencephalic neurons produced a significant intoxication of dopaminergic neurons (around −33% of TH neurons) in all the experiments (control, FIG. 1).

BDNF was used as a positive control. 1 hour of BDNF pre-treatment at 1.85 nM significantly protected the dopaminergic neurons from this 6-OHDA injury.

As shown in FIG. 1, baclofen-acamprosate successfully protects dopaminergic neurons from 6-OHDA intoxication, in a dose dependent manner.

b. Baclofen and acamprosate combinations are efficient in protecting neuronal cells from amyloid β mitochondrial poisoning and subsequent oxidative stress.

Amyloid β is known as a mitochondrial toxin triggering mitochondrial collapse and also causing oxidative stress. Interestingly amyloid β is found in drusen whose accumulation is considered as an early sign of AMD.

Inventors have observed that baclofen and acamprosate combinations are efficient in protecting against amyloid β induced oxidative stress and mitochondrial poisoning. Indeed methionine sulfoxide levels (MetO, a marker of oxidative stress status of the cells) and cytochrome C (release of cytochrome C within cytoplasm is a marker of mitochondrial impairment) levels are significantly reduced within nervous cells cultured in presence of amyloid β but when treated with baclofen and acamprosate compositions. Noteworthy, CytC has also been described as a potential marker for retinal cell degeneration by uv/vis spectroscopic imaging [27] thereby stressing the importance of the oxidative and mitochondrial dysfunction in AMD.

Cortical Cell Culture

Rat cortical neurons were cultured as described by Singer et al., 1999 [28]. Briefly pregnant female rats of 15 days gestation were killed by cervical dislocation (Rats Wistar) and the fetuses were removed from the uterus. The cortex were removed and placed in ice-cold medium of Leibovitz (L15) containing 2% of Penicillin 10.000 U/ml and Streptomycin 10 mg/ml and 1% of bovine serum albumin (BSA). Cortex were dissociated by trypsin (0.05%) for 20 min at 37° C. The reaction was stopped by the addition of Dulbecco's modified Eagle's medium (DMEM) containing DNase1 grade II (0.1 mg/mL) and 10% of fetal calf serum (FCS). Cells were then mechanically dissociated by 3 serial passages through a 10 ml pipette. Cells were then centrifuged at 515×g for 10 min at 10° C. The supernatant was discarded and the pellet of cells will be re-suspended in a defined culture medium consisting of Neurobasal supplemented with B27 (2%), L-glutamine (0.2 mM), 2% of PS solution and 10 ng/mL of BDNF. Viable cells were counted in a Neubauer cytometer using the trypan blue exclusion test. The cells were seeded at a density of 30 000 cells/well (for CytC investigation) or 15 000 cells/well (for MetO evaluation) in 96 well-plates (wells are pre-coated with poly-L-lysine (10 µg/mL) and were cultured at 37° C. in a humidified air (95%)/CO2 (5%) atmosphere. After 11 days of culture, cortical neurons were intoxicated with human amyloid-$\beta_{1-42}$ peptide at 1.25 µM during 4 hours.

Human Amyloid-β1-42 Intoxication

Human $A\beta_{1-42}$ was reconstituted in define culture medium at 40 µM (mother solution) and will be slowly shacked at 37° C. for 3 days in dark. The control medium was prepared in the same conditions.

After 3 days, 1.25 µM of this amyloid peptide was incubated during 4 hours on cortical neurons, diluted in control medium.

BDNF at 50 ng/mL was used as a positive control. BDNF was solved in culture medium and pre-incubated for 1 h before the amyloid $\beta_{1-42}$ application. Test mix (baclofen 80 nM and acamprosate 0.32 nM) was pre-incubated for 1 h before the amyloid $\beta_{1-42}$ application.

Measurements of Oxidative Stress: MetO Assay

After 4 hours of intoxication, cells were fixed by a cold solution of ethanol (95%) and acetic acid (5%) for 5 min. The cells were then permeabilized and non-specific sites were blocked with a solution of phosphate buffered saline (PBS; PanBiotech) containing 0.1% of saponin (Sigma) and 1% fetal calf serum (FCS) for 15 min at room temperature. Then, cells were incubated with monoclonal antibody anti microtubule-associated-protein 2 (MAP-2; Sigma). This antibody stains specifically cell bodies and neurites of neurons. A co-staining was done using Polyclonal MetO primary antibody (Euromedex).

These antibodies were revealed with Alexa Fluor 488 goat anti-mouse IgG (Molecular probe) and with Alexa Fluor 568 goat anti rabbit IgG (Molecular probe). Nuclei of neurons will be labeled by a fluorescent marker (Hoechst solution, SIGMA).

Measurements of Oxidative Stress and Mitochondrial Integrity:Cytoplasmic Cytochrome C (CytoC) Assay This assay was essentially performed as above, except that a polyclonal CytoC primary antibody (Abcam) was used to detect cytoplasmic cytochrome C.

Statistical Analysis

Data are expressed in percentage of control conditions (no intoxication, no amyloid=100%) in order to express the amyloid injury. All values are expressed as mean+/−SEM (s.e. mean) of the 3 cultures (n=6 wells per condition). Analysis was performed using an ANOVA followed by the Dunnett's and PLSD Fisher's test when it was allowed (Statview software version 5.0).

Results

Results are summarized in table 2. Compositions of the invention are efficient in protecting nervous cells from oxidative stress and mitochondrial dysfunction which are components of AMD pathogenesis.

Figure 2:
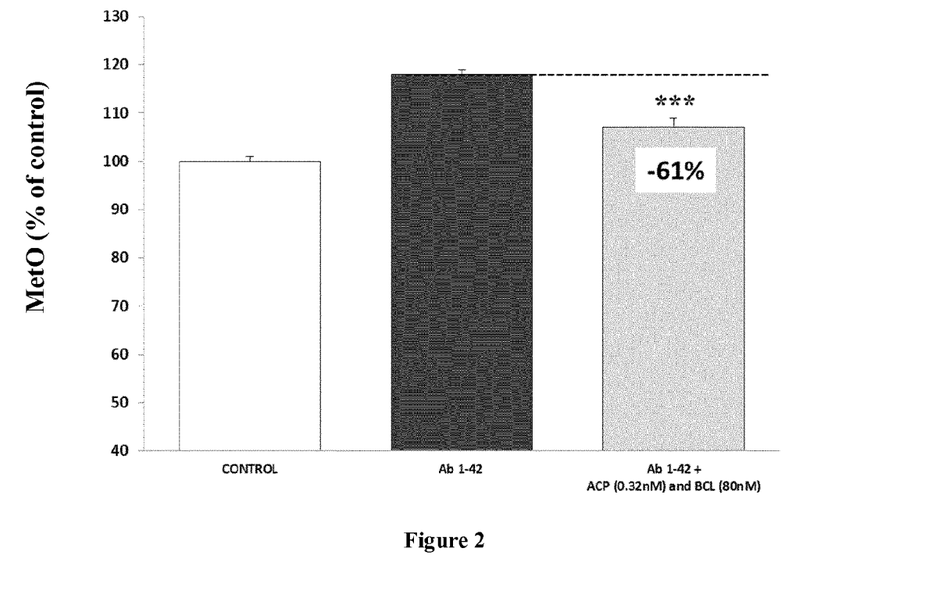
FIG. 2: Effect of baclofen and acamprosate combination therapy against $A\beta_{1-42}$ induced oxidative stress. Baclofen and acamprosate therapy is efficient in protecting neuronal cells from oxidative stress as shown by the observed significant decrease in methionine sulfoxide levels in treated cells (grey bar, −61%) when compared to non-treated intoxicated cells (black bar). (***p<0.0001 significantly different from $A\beta_{1-42}$ intoxicated cells (ANOVA+Dunnett post hoc test))
Figure 3:
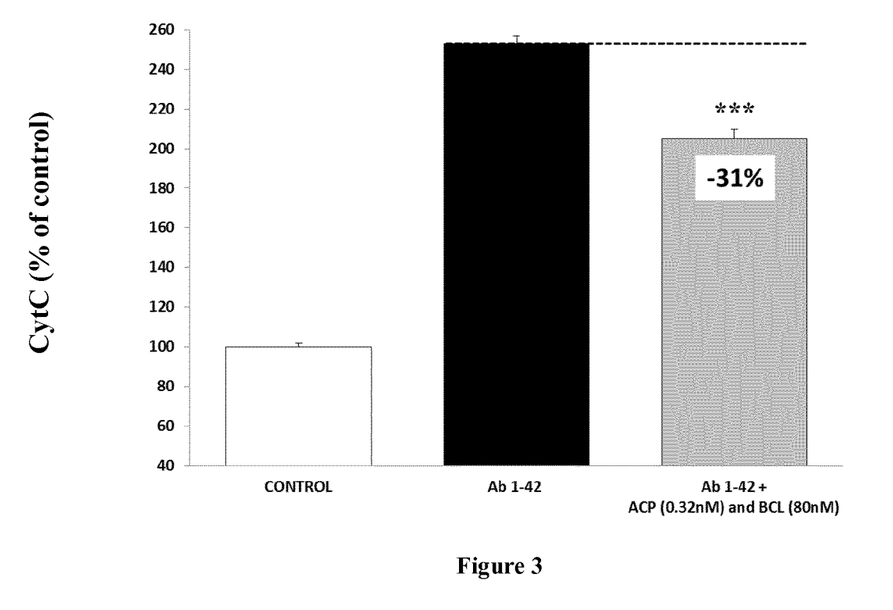
FIG. 3: Effect of baclofen and acamprosate combination therapy against $A\beta_{1-42}$ induced mitochondrial dysfunction. Baclofen and acamprosate therapy is efficient in protecting neuronal cells from mitochondrial impairment as shown by the observed significant decrease of cytochrome C cytoplasmic levels in treated cells (grey bar, −31%) when compared to non-treated intoxicated cells (black bar). (***p<0.0001 significantly different from $A\beta_{1-42}$ intoxicated cells (ANOVA+Dunnett post hoc test))

A significant decrease (−61%) in cell methionine sulfoxide residues is noticed in $A\beta_{1-42}$ intoxicated neuronal cells when pretreated with baclofen and acamprosate combination (FIG. 2). This is confirmed by the decrease of cytochrome C release in the cytoplasm of the treated intoxicated cells when compared to non-treated intoxicated cells, which is the signature of an inhibition of the mitochondrial impairment (FIG. 3). Hence, baclofen and acamprosate composition efficiently protect neuronal cells from oxidative stress and mitochondrial dysfunction observed in AMD.

II. In Vivo Inhibition of Choroidal Angiogenic Lesions

Choroidal neovascularisation (CNV) is a major cause of severe central vision loss in patient with wet AMD. Effect of combinations of the invention on wet AMD was assessed in a mouse model for choroidal angiogenesis.

In this model, on Day 0 choroidal burns are induced by argon laser treatment to the eyes of rats (6 burns per eye).

Reference compound, and compounds and combinations of the invention are administered orally one day before the lesions or at D0.

On Days 14 and 21 of treatment, quantification of leakage in each lesion is measured by fluorescein angiography: Anesthetized animals received subcutaneous injection of Fluorescein Sodium. Images are taken with a retinal angiograph and the intensity of fluorescein staining of each lesion is graded using a leakage score (0=no leakage to 3=strong leakage) (24).

On Day 23, animals are sacrificed and retinas are collected. The volume of each neovascular lesion is measured using FITC labeled Isolectine B4 (detection with a ZIS apotome microscope).

Baclofen and acamprosate combination is effective in decreasing neovascular lesions leakage and in limiting their extent as mentioned in table 2.

III. In Vivo Improvement of Retinal Function and Protection of Retina Tissues Toward Retinal Degeneration Blue light has been shown to cause a photochemical reaction that produces free radicals in the RPE, the rods and cones. It is believed that this free radicals production finally results in clogging up the macula's maintenance system and to producing dry macular degeneration (25).

Compounds and combinations of the invention are tested in a rat model of blue light induced retinal degeneration. Their efficacy in protecting toward retinal degeneration is assessed by electroretinography which measures electrical potentials contributed by different cell types within the retina in response to a stimulus.

Briefly, at D0 dark adapted Sprague Dawley rats are exposed during 6 hours to the intense blue fluorescent light.

Animals are dosed with baclofen and acamprosate combination, administered per os, from 2 days or one day before the lesions or at least at D0. Retinal degeneration is evaluated by comparing the amplitude of a-wave of the ERG measured, before, and at days D7 and D14 from the induction.

On Day 14 rats are sacrificed and the eyes are collected; electrophysiological study is completed by a histological measure of the thickness of the retinal outer nuclear layer (ONL) which is also a marker of retinal integrity.

Results are summarized in table 2. In the animals treated with baclofen and acamprosate combination, there is a significant increase in a-wave amplitude of the ERG measured after blue light exposition (D7-D14), in comparison with non-treated animals. This improvement in the electrophysiological functions is correlated with the observation that, in treated animals, ONL is globally thicker than in non-treated animals. These results show that the combinations of the invention are efficient in protecting eyes from retinal degeneration.

REFERENCES

1 Lim L S, Mitchell P, Seddon J M, Holz F G & Wong T Y (2012) Age-related macular degeneration. *Lancet* 379, 1728-38.

2 Wu K H C, Madigan M C, Billson F A & Penfold P L (2003) Differential expression of GFAP in early v late AMD: a quantitative analysis. *The British journal of ophthalmology* 87, 1159-66.

3 Wormald R, Evans J, Smeeth L & Henshaw K (2007) Photodynamic therapy for neovascular age-related macular degeneration. *Cochrane database of systematic reviews (Online)*, CD002030.

4 Semeraro F, Morescalchi F, Parmeggiani F, Arcidiacono B & Costagliola C (2011) Systemic adverse drug reactions secondary to anti-VEGF intravitreal injection in patients with neovascular age-related macular degeneration. *Current vascular pharmacology* 9, 629-46.

5 Jeganathan V S E & Verma N (2009) Safety and efficacy of intravitreal anti-VEGF injections for age-related macular degeneration. *Current opinion in ophthalmology* 20, 223-5.

6 Ettmayer P, Amidon G L, Clement B & Testa B (2004) Lessons learned from marketed and investigational prodrugs. *Journal of medicinal chemistry* 47, 2393-404.

7 Beaumont K, Webster R, Gardner I & Dack K (2003) Design of ester prodrugs to enhance oral absorption of poorly permeable compounds: challenges to the discovery scientist. *Current drug metabolism* 4, 461-85.

8 Heimbach T, Oh D M, Li L Y, Rodriguez-Hornedo N, Garcia G & Fleisher D (2003) Enzyme-mediated precipitation of parent drugs from their phosphate prodrugs. *International journal of pharmaceutics* 261, 81-92.

9 Yang C Y, Dantzig A H & Pidgeon C (1999) Intestinal peptide transport systems and oral drug availability. *Pharmaceutical research* 16, 1331-43.

10 Steffansen B, Nielsen C U, Brodin B, Eriksson A H, Andersen R & Frokjaer S (2004) Intestinal solute carriers: an overview of trends and strategies for improving oral drug absorption. *European journal of pharmaceutical sciences: official journal of the European Federation for Pharmaceutical Sciences* 21, 3-16.

11 Stella V J (2007) *Prodrugs: challenges and rewards.* Springer Singapore Pte. Limited.

12 Wermuth C G (2011) *The Practice of Medicinal Chemistry* Elsevier Science.

13 Stella V J (2004) Prodrugs as therapeutics. *Expert Opinion on Therapeutic Patents* 14, 277-280.

14 Higuchi T & Stella V J (1975) *Pro-drugs as Novel Drug Delivery System*, ACS Sympos American Chemical Society, Washington, D.C.

15 Stella V J & Nti-Addae K W (2007) Prodrug strategies to overcome poor water solubility. *Advanced drug delivery reviews* 59, 677-94.

16 Roche E B (1977) *Design of biopharmaceutical properties through prodrugs and analogs: a symposium*, American P The Academy, Washington, D.C.

17 Pezron I, Mitra A K, Duvvuri S & Tirucherai G S (2002) Prodrug strategies in nasal drug delivery. *Expert Opinion on Therapeutic Patents* 12, 331-340.

18 Lal R, Sukbuntherng J, Tai E H L, Upadhyay S, Yao F, Warren M S, Luo W, Bu L, Nguyen S, Zamora J, Peng G, Dias T, Bao Y, Ludwikow M, Phan T, Scheuerman R A, Yan H, Gao M, Wu Q Q, Annamalai T, Raillard S P, Koller K, Gallop M A & Cundy K C (2009) Arbaclofen placarbil, a novel R-baclofen prodrug: improved absorption, distribution, metabolism, and elimination properties compared with R-baclofen. *The Journal of pharmacology and experimental therapeutics* 330, 911-21.

19 Xu F, Peng G, Phan T, Dilip U, Chen J L, Chernov-Rogan T, Zhang X, Grindstaff K, Annamalai T, Koller K, Gallop M A & Wustrow D J (2011) Discovery of a novel potent GABA(B) receptor agonist. *Bioorganic & medicinal chemistry letters* 21, 6582-5.
20 Leach A R & Gillet V J *An Introduction to Chemoinformatics* (Springer-Verlag New York Inc, ed.).
21 Rahman S A, Bashton M, Holliday G L, Schrader R & Thornton J M (2009) Small Molecule Subgraph Detector (SMSD) toolkit. *Journal of cheminformatics* 1, 12.
22 Stahl P H & Wermuth C G (2008) *Pharmaceutical Salts* Wiley.
23 Hanafi R, Mosad S, Abouzid K, Niess R & Spahn-Langguth H (2011) Baclofen ester and carbamate prodrug candidates: a simultaneous chromatographic assay, resolution optimized with DryLab. *Journal of pharmaceutical and biomedical analysis* 56, 569-76.
24 Stone W L, Farnsworth C C & Dratz E A (1979) A reinvestigation of the fatty acid content of bovine, rat and frog retinal rod outer segments. *Experimental eye research* 28, 387-97.
25 Liang F-Q & Godley B F (2003) Oxidative stress-induced mitochondrial DNA damage in human retinal pigment epithelial cells: a possible mechanism for RPE aging and age-related macular degeneration. *Experimental eye research* 76, 397-403.
26 Schinelli S, Zuddas A, Kopin I J, Barker J L & Di Porzio U (1988) 1-Methyl-4-phenyl-1,2,3,6-tetrahydropyridine metabolism and 1-methyl-4-phenylpyridinium uptake in dissociated cell cultures from the embryonic mesencephalon. *Journal of neurochemistry* 50, 1900-7.
27 Hollmach J, Schweizer J, Steiner G, Knels L, Funk R H W, Thalheim S & Koch E (2011) Characterization of cytochrome c as marker for retinal cell degeneration by uv/vis spectroscopic imaging. In *Clinical and Biomedical Spectroscopy and Imaging II* (Ramanujam N and P, ed), p. 80871F. OSA, Washington, D.C.
28 Singer C A, Figueroa-Masot X A, Batchelor R H & Dorsa D M (1999) The mitogen-activated protein kinase pathway mediates estrogen neuroprotection after glutamate toxicity in primary cortical neurons. *The Journal of neuroscience: the official journal of the Society for Neuroscience* 19, 2455-63.

The invention claimed is:

1. A method for treating a macular degeneration disorder in a subject in need thereof, or for inhibiting or stopping the progression of said disorder, comprising administering to the subject a composition containing baclofen and acamprosate, or salts(s) thereof, or prodrugs(s) thereof, or sustained release formulation(s) thereof.

2. The method of claim 1, wherein the macular degeneration disorder is selected from dry or wet Age-related Macular Degeneration (AMD), Stargardt disease, early or adult onset vitelliform macular dystrophies, and diabetic retinopathy.

3. The method of claim 1, wherein the subject has been diagnosed as bearing drusen or retinal pigmentory changes.

4. The method of claim 1, for stopping or retarding the evolution from early AMD to wet or dry forms of AMD in a patient in need thereof.

5. The method of claim 1, wherein the subject is experiencing retinal degeneration or abnormal ocular angiogenesis.

6. The method of claim 1, wherein the composition further comprises a pharmaceutically acceptable carrier or excipient.

7. The method of claim 1, wherein baclofen and acamprosate are formulated or administered together, separately or sequentially.

8. The method of claim 1, wherein said composition is administered repeatedly to the subject.

9. The method of claim 1, wherein a calcium salt of acamprosate is used.

10. A method for treating a macular degeneration disorder in a subject in need thereof, or for inhibiting or stopping the progression of said disorder in a subject in need thereof, the method comprising: separately or simultaneously administering to said subject baclofen, or a salt thereof, or a prodrug thereof, or sustained release formulation thereof, and acamprosate, or a salt thereof, or a prodrug thereof, or sustained release formulation thereof.

* * * * *